United States Patent
Carbo, Jr. et al.

(10) Patent No.: US 9,080,931 B2
(45) Date of Patent: Jul. 14, 2015

(54) METHOD OF IMPACT TESTING USING MOUNT ASSEMBLY WITH DEFORMABLE MEMBER

(71) Applicant: Nike, Inc., Beaverton, OR (US)

(72) Inventors: Jorge E. Carbo, Jr., Aloha, OR (US); Martine I. V. Mientjes, Beaverton, OR (US); Jeffrey D. Allison, Lake Oswego, OR (US)

(73) Assignee: NIKE, Inc., Beaverton, OR (US)

( * ) Notice: Subject to any disclaimer, the term of this patent is extended or adjusted under 35 U.S.C. 154(b) by 187 days.

(21) Appl. No.: 13/789,000

(22) Filed: Mar. 7, 2013

(65) Prior Publication Data

US 2014/0083165 A1      Mar. 27, 2014

Related U.S. Application Data

(63) Continuation-in-part of application No. 13/604,433, filed on Sep. 5, 2012.

(51) Int. Cl.
| | |
|---|---|
| *G01M 7/00* | (2006.01) |
| *G01N 3/30* | (2006.01) |
| *G01M 7/08* | (2006.01) |
| *G09B 23/30* | (2006.01) |
| *G01L 5/00* | (2006.01) |
| *F41H 1/02* | (2006.01) |

(52) U.S. Cl.
CPC ............... *G01N 3/30* (2013.01); *G01L 5/0052* (2013.01); *G01M 7/08* (2013.01); *G09B 23/30* (2013.01); *F41H 1/02* (2013.01)

(58) Field of Classification Search
CPC .......... G01L 5/0052; G01M 7/08; G01N 3/30
USPC .................. 73/12.01, 12.04, 12.09, 12.06
See application file for complete search history.

(56) References Cited

U.S. PATENT DOCUMENTS

| | | | |
|---|---|---|---|
| 3,331,236 | A | 7/1967 | Payne et al. |
| 3,557,471 | A | 9/1968 | Payne et al. |
| 3,755,920 | A | 9/1973 | Smrcka |
| 4,349,339 | A | 9/1982 | Daniel |
| 4,850,877 | A | 7/1989 | Mason et al. |

(Continued)

FOREIGN PATENT DOCUMENTS

| | | |
|---|---|---|
| FR | 2901881 A1 | 12/2007 |
| WO | 2012085054 A1 | 6/2012 |

OTHER PUBLICATIONS

Test Method and Standard Performance Specification for Newly Manufactured Soccer Shin Guards, prepared by National Operating Committee on Standards for Athletic Equipment, accessed Jul. 10, 2012 at: http://www.nocsae.org/standards/pdfs/ND090-06m07-%20Mfr'd%20Soccer%20Shin%20Guards%20Std%20performance.pdf.

(Continued)

*Primary Examiner* — Max Noori
(74) *Attorney, Agent, or Firm* — Shook, Hardy & Bacon L.L.P.

(57) ABSTRACT

A method of impact testing an article of protective equipment includes mounting the article of protective equipment on a deformable member. The method also includes impacting the article of protective equipment with an impact object. Moreover, the method includes detecting an effect of impact on the deformable member due to impacting the article of protective equipment with the impact object.

16 Claims, 4 Drawing Sheets

(56) References Cited

U.S. PATENT DOCUMENTS

| | | | |
|---|---|---|---|
| 5,696,325 A * | 12/1997 | Coucke et al. | 73/595 |
| 5,716,302 A | 2/1998 | Andersson | |
| 5,850,033 A | 12/1998 | Mirzeabasov et al. | |
| 6,318,148 B1 * | 11/2001 | Alkonis | 73/12.09 |
| 6,742,381 B2 * | 6/2004 | Maeno | 73/11.01 |
| 6,833,924 B2 | 12/2004 | Love et al. | |
| 6,923,081 B2 | 8/2005 | Krstic | |
| 6,986,290 B2 | 1/2006 | Konosu | |
| 7,239,817 B2 * | 7/2007 | Kaneko et al. | 399/45 |
| 7,509,835 B2 | 3/2009 | Beck | |
| 7,800,505 B2 | 9/2010 | Pietersen | |
| 7,900,499 B2 * | 3/2011 | Zhang | 73/12.13 |
| 7,930,920 B2 | 4/2011 | Le Carpentier | |
| 2002/0112526 A1 * | 8/2002 | Mattes | 73/12.09 |
| 2007/0160966 A1 | 7/2007 | Cohen et al. | |
| 2010/0186134 A1 | 7/2010 | Hunter et al. | |

OTHER PUBLICATIONS

The successful supply of PPE—an essential guide; http://www.satrappeguide.com/EN1621.php; accessed on Nov. 12, 2013.
Non-Final Office Action dated Jul. 8, 2014 in U.S. Appl. No. 13/604,433, 6 pages.
Notice of Allowance dated Nov. 24, 2014 in U.S. Appl. No. 13/604,433, 5 pages.
International Search Report with Written Opinion dated Feb. 5, 2014 in Application No. PCT/US2013/057987, 12 pages.

* cited by examiner

Impact Force = F = mass · acceleration

Pressure = F/Y

METHOD OF IMPACT TESTING USING MOUNT ASSEMBLY WITH DEFORMABLE MEMBER

CROSS REFERENCE TO RELATED APPLICATION

This application is a continuation-in-part of U.S. patent application Ser. No. 13/604,433, filed on Sep. 5, 2012, which is hereby incorporated by reference in its entirety.

FIELD

The present disclosure relates to impact testing and, more particularly, to a method of impact testing using a mount assembly with a deformable member.

BACKGROUND

This section provides background information related to the present disclosure which is not necessarily prior art.

Athletes often wear protective pads, plates, guards, masks, and other protective articles of apparel. For instance, football players (players of American-style football) often wear thigh guards that are worn to protect the player's thighs. As such, the thigh area can be protected from contusions or other injuries that could otherwise occur during play.

These articles of apparel can be tested on a compression testing machine, such as an impact testing machine. These tests can reveal the compressive strength of the apparel, the impact attenuation of the apparel, impact durability of the apparel, the flexibility of the apparel, or other characteristics of the apparel. This data can be used to evaluate the suitability of the apparel for protecting a wearer during use.

SUMMARY

This section provides a general summary of the disclosure, and is not a comprehensive disclosure of its full scope or all of its features.

A method of impact testing an article of protective equipment is disclosed. The method includes mounting the article of protective equipment on a deformable member. The method also includes impacting the article of protective equipment with an impact object. Moreover, the method includes detecting an effect of impact on the deformable member due to impacting the article of protective equipment with the impact object.

A method of impact testing an article of protective equipment is also disclosed that includes mounting the article of protective equipment on a deformable member that is supported by a substantially rigid core member. The method further includes impacting the article of protective equipment with an impact object to thereby resiliently deform the deformable member. Moreover, the method includes detecting a distribution of pressure on an outer surface of the deformable member due to impacting the article of protective equipment with the impact object.

Additionally, a method of impact testing an article of protective equipment is disclosed. The method includes mounting the article of protective equipment on a deformable member that is supported by a substantially rigid core member. The method further includes impacting the article of protective equipment with an impact object at a predetermined impact energy during a first cycle to thereby drive the article of protective equipment toward the deformable member and to resiliently deform the deformable member. The method additionally includes detecting a first distribution of pressure on an outer surface of the deformable member due to impacting the article of protective equipment with the impact object during the first cycle. Moreover, the method includes impacting the article of protective equipment with the impact object at the predetermined impact energy during a second cycle to thereby drive the article of protective equipment toward the deformable member and to resiliently deform the deformable member. Still further, the method includes detecting a second distribution of pressure on the outer surface of the deformable member due to impacting the article of protective equipment with the impact object during the second cycle.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
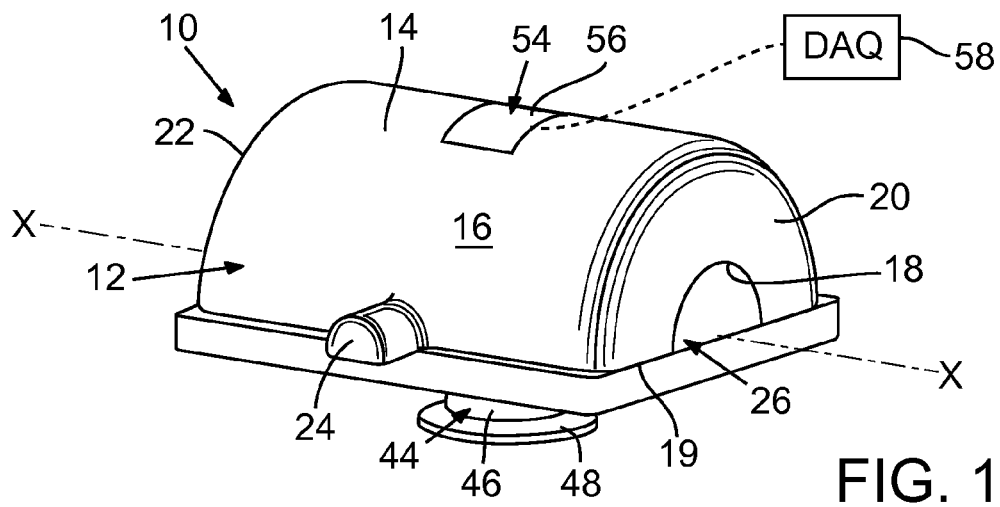
FIG. 1 is a perspective view of a mount assembly used for impact or other compression testing of protective equipment according to various exemplary embodiments of the present disclosure.
Figure 2:
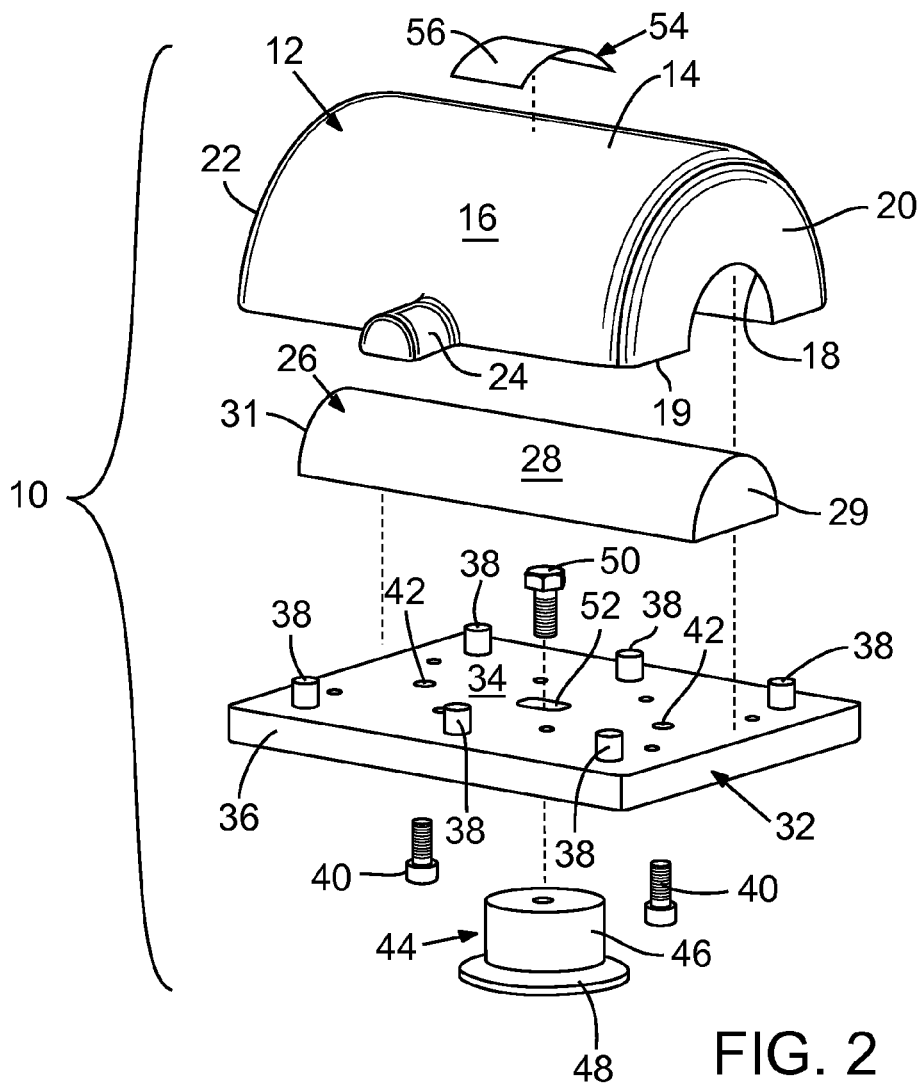
FIG. 2 is an exploded perspective view of the mount assembly of FIG. 1.
Figure 3:
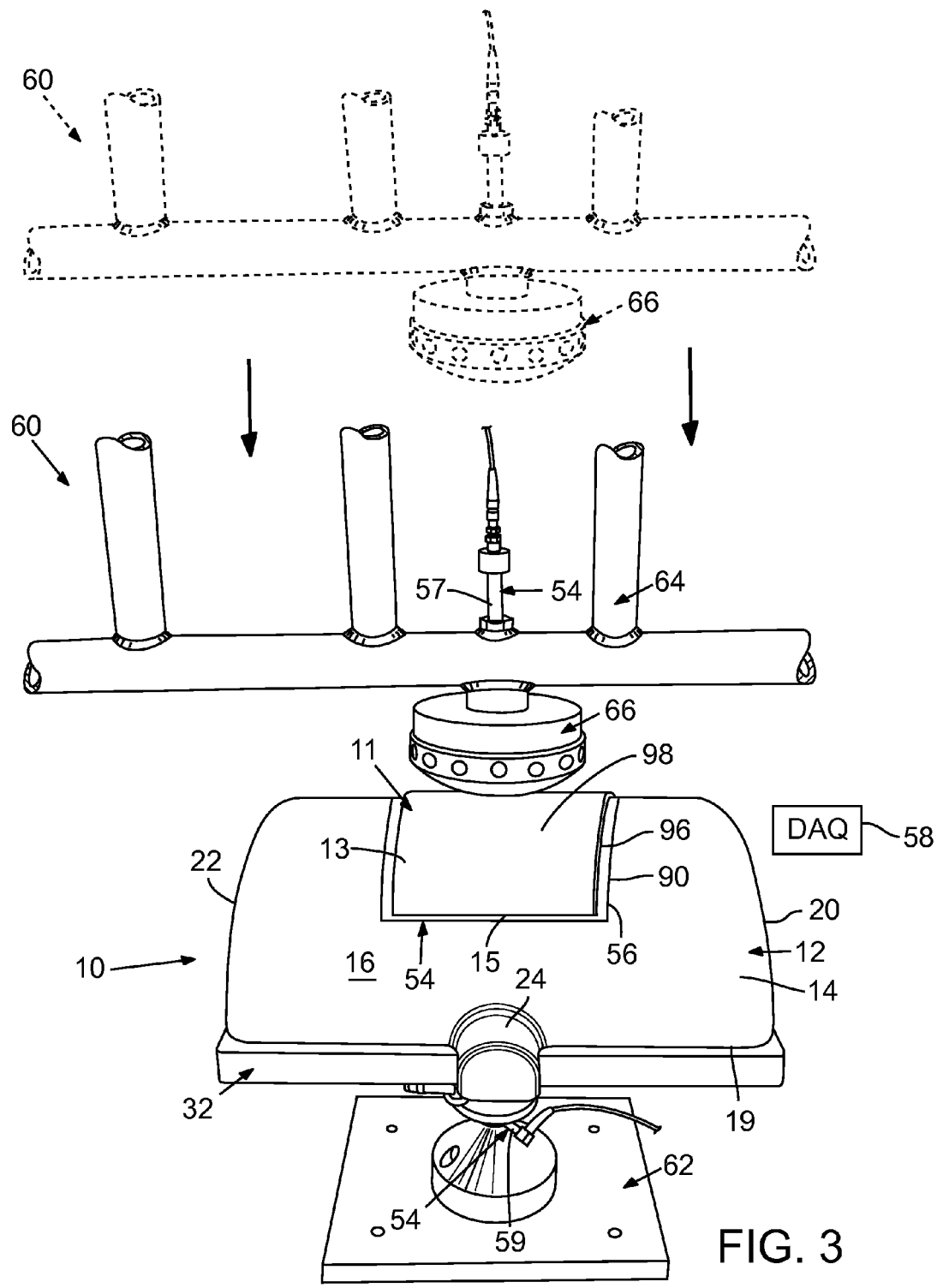
FIG. 3 is a perspective view of the mount assembly of FIG. 1 shown during an exemplary impact test of protective equipment.

Referring initially to FIGS. 1-3, a mount assembly 10 is illustrated. As will be discussed, the mount assembly 10 can be used for compression testing of an article of apparel 11 (FIG. 3). It will be appreciated that the term "compression testing" is defined broadly herein to include tests in which compression is applied to the apparel 11 for relatively large amounts of time (e.g., pressing and holding the apparel 11 under compressive loads for one or more seconds) and to include tests in which compression is applied for relatively small amounts of time (e.g., impact testing wherein compressive loads are applied to the apparel 11 nearly instantaneously).

The mount assembly 10 can be used for testing any suitable article of apparel 11. For instance, the apparel 11 can be protective apparel (i.e., wearable protective equipment), such as a thigh guard for an athlete (e.g., a football player), or other type. As such, data can be gathered regarding how the article of apparel 11 will perform when worn during sporting or other activities.

Also, as will be discussed, the mount assembly 10 can perform under impact or other compressive loads in a manner that simulates an anatomical body part of the wearer of the apparel 11. For instance, the mount assembly 10 can simulate an anatomical thigh (i.e., an upper leg between the knee and hip joints) of a wearer such that the mount assembly 10 is configured as an "artificial thigh." Thus, as will be discussed in detail, the assembly 10 can include a core member 26 that simulates an anatomical femur bone, and the assembly 10 can include a deformable member 12 that simulates the anatomical soft tissue (e.g., skin, musculature, connective tissue, etc.) surrounding a femur. Accordingly, the mount assembly 10 can increase the accuracy of impact or other compression testing so that researchers can better evaluate the characteristics of the article of apparel 11.

As will be discussed, the deformable member 12 and core member 26 of the mount assembly 10 can be shaped similar to an anatomical thigh (more specifically, an anterior half of the thigh skin, muscles and other soft tissue as well as the anterior half of the femur). Also, the members 12, 26 of the mount assembly 10 can also have mechanical characteristics (e.g., modulus of elasticity, compression characteristics, resiliency, elasticity, durometer, stiffness, resistance to resilient deformation, toughness etc.) that are similar to the corresponding parts of an anatomical thigh. Moreover, the deformable member 12 can have elastic and/or plastic deformation characteristics that substantially correspond to those characteristics of an anatomical thigh. However, the mount assembly 10 of the present disclosure can be shaped and/or can be configured to exhibit the characteristics of any other anatomical body part without departing from the scope of the present disclosure. For instance, the mount assembly 10 can be configured to simulate a shoulder, a lower leg, a lower back, the buttocks, or other anatomical body part.

Still further, the mount assembly 10 will be discussed as being configured for impact testing the article of apparel 11 and for evaluating the protection provided by the apparel 11 for the wearer's body. However, as mentioned above, the mount assembly 10 could be configured for any other type of compression testing. The mount assembly 10 could also be configured for other testing, such as vibration testing, etc.

In the exemplary embodiments shown, the deformable member 12 can be a unitary body of material (i.e., monolithic). The deformable member 12 can include a main body 14 that has a generally C-shaped cross section and that extends along a straight longitudinal axis X (FIG. 1). The main body 14 can also include a convex outer surface 16. The outer surface 16 can have a radius (measured from the axis X) that is substantially constant along its entire length along the axis X. In the embodiments shown, the outer surface 16 is curved about the axis X only and is only convexly curved. However, the outer surface 16 could be more complexly curved (e.g., about multiple axes, convex and concavely curved, etc.). Also, the outer surface 16 could be flat in certain areas. Additionally, the radius of the outer surface 16 can vary along the axis X (e.g., such that the outer surface 16 tapers along the axis X, similar to an anatomical thigh, etc.).

The outer surface 16 can be configured to support the article of apparel 11 thereon as shown in FIG. 3. Therefore, the outer surface 16 can be shaped in a way that corresponds and/or is substantially complimentary to that of the article of apparel 11. For instance, as shown in FIG. 3, the article of apparel 11 can be thin and curved and can include an inner surface 13, an outer surface 15, and an outer peripheral edge 96. The inner surface 13 is concave and worn against the thigh of the wearer; therefore, the outer surface 16 of the main body 14 can be convex and can have a radius that substantially matches or otherwise compliments that of the inner surface 13 to substantially simulate the fit of the article of apparel 11 to the wearer's thigh. Stated differently, the outer surface 16 of the deformable member 12 can be configured to nestingly receive and fit to the inner surface 13 of the article of apparel 11.

As shown in FIG. 2, the main body 14 can further include a concave inner surface 18 that also has a radius that is substantially constant along its entire length. The radial distance between the inner surface 18 and the outer surface 16 (i.e., the thickness of the main body 14) can be of any suitable value. Moreover, the main body 14 can have a substantially flat (planar) first end 20 and a substantially flat (planar) second end 22. The ends 20, 22 can be substantially perpendicular to the axis X. The length of the main body 14 defined between the first and second ends 20, 22 can have any suitable value. Moreover, the main body 14 can have a substantially flat (planar) bottom surface 19 that is bisected by the concave inner surface 18.

The deformable member 12 can further include at least one projection 24. The projection 24 can have a D-shaped cross section and can project transversely away from the longitudinal axis X and away from the main body 14. In the embodiments illustrated, the projection 24 projects perpendicularly away from the axis X, but the projection 24 could project away from the axis X at any suitable angle. Furthermore, the projection 24 could curve longitudinally in some embodiments. Also, although only one projection 24 is illustrated in FIGS. 1-3, it will be appreciated that another projection 24 can project away from the opposite side of the main body 14. Moreover, the deformable member 12 could include any number of projections 24 at any suitable location without departing from the scope of the present disclosure. As will be discussed, the projection 24 can be configured for mounting the apparel 11 or for any suitable purpose.

The deformable member 12 can be made out of any suitable material. For instance, the deformable member 12 can include silicone material or other elastomeric material that is molded in any suitable molding process. As such, as will be discussed in detail, impact testing can cause the deformable member to resiliently deform from the neutral state shown in FIGS. 1-3.

Further, the core member 26 can be substantially rigid. The core member 26 can be made out of or can otherwise include a substantially rigid material, such as steel, aluminum, ceramic material, composite material, etc. The core member 26 can have a D-shaped cross section that extends along the axis X. The core member 26 can include a convex upper surface 28 and a substantially flat bottom surface 30. The core member 26 can also include a substantially flat first end 29 and a substantially flat second end 31. The first and second ends 29, 31 can be substantially perpendicular to the axis X.

The deformable member 12 can receive the core member 26 such that the deformable member 12 arcs around the core member 26 and such that the inner surface 18 of the main body 14 abuts the upper surface 28 of the core member 26. The core member 26 can be substantially coaxial with the deformable member 12. The deformable member 12 and the core member 26 can, together, have a semi-circular cross section. In the embodiments illustrated, for example, the deformable member 12 and core member 26 can cooperate to define approximately 50% of a circular cross section (i.e., span 180 degrees) to generally correspond in shape to an anterior section of the thigh. However, the cross section could be configured to resemble that of the entire (i.e., anterior and posterior) thigh or other desired body part.

Additionally, the mount assembly 10 can include a base plate 32 (FIG. 2). The base plate 32 can be substantially flat and can have any suitable thickness. The base plate 32 can include an upper surface 34 and a lower surface 36. The base plate 32 can be used to support the deformable member 12 and the core member 26. Thus, the upper surface 34 can abut both the bottom surface 30 of the core member 26 and the bottom surface 19 of the main body 14 of the deformable member 12. Also, a plurality of alignment pins 38 or other fastening elements can extend into both the base plate 32 and the deformable member 12 through the upper surface 34 and the bottom surface 19, respectively. Similarly, a plurality of fasteners 40 (e.g., bolts) can fasten to both the core member 26 and the base plate 32 (e.g., via corresponding through-holes 52 defined in the base plate 32).

Also, the base plate 32 can be used to attach the mount assembly 10 to an impact testing device 60 (FIG. 3). As shown in FIGS. 1 and 2, the mount assembly 10 can include a mount 44 that includes a cylindrical stem 46 and a radially projecting lower flange 48. A fastener 50 (e.g., a bolt, etc.) can extend through a through-hole 52 to fasten to the stem 46. The stem 46 and flange 48 can be received and fixed within a complementary opening in a frame of the impact testing device 60 (FIG. 3).

In some embodiments, the core member 26 and the base plate 32 can be used to partially form the deformable member 12. For instance, the core member 26 and base plate 32 can be attached together and placed over a mold or trough (not shown) that has a cavity with an inner surface corresponding in shape to the outer surface 16 of the deformable member 12. Then, flowable elastomeric material (e.g., silicone) can be introduced into the cavity and cured. Thus, the outer surface 16 of the deformable member 12 can be molded and shaped against the inner surface of the cavity of the mold, the inner surface 18 can be molded and shaped against the upper surface 28 of the core member 26, and the bottom surface 19 can be molded and shaped against the upper surface 34 of the base plate 32. As such, the deformable member 12 can fit closely and can conform to the shape of the core member 26 and the base plate 32.

Still further, the mount assembly 10 can include one or more sensors 54 that are operable for detecting the effects of impacting or otherwise compressing the apparel 11, the deformable member 12, and/or the core member 26 together during impact testing or other compression testing. It will be appreciated that the assembly 10 can include any number of sensors 54 of any suitable type. For instance, one or more sensors 54 can detect a load on the deformable member 12 due to impacting the apparel 11. It will be appreciated that the term "load" is used generally herein to include impact force, pressure (impact force divided by area of impact), dynamic pressure (pressure change over a time period), impact energy, stress, strain, bending moment, torque, and the like. Also, the sensors 54 can be operable for detecting acceleration, velocity, and other characteristics of the testing devices. Various sensors 54 that could be used with the assembly 10 will be discussed in detail below.

Referring now to FIG. 3, various embodiments of the mount assembly 10 will be discussed as incorporated in an impact testing device 60, an example of which is partially shown. Generally, the device 60 can support the mount assembly 10 and can support an impactor 66 (impact object) for movement relative to the mount assembly 10. Also, the device 60 can support the impactor 66 such that the impactor 66 can impact the apparel 11, which is supported atop the mount assembly 10 as shown in FIG. 3.

As shown, the device 60 can include a base 62 (i.e., anvil). The stem 46 and lower flange 48 of the mount assembly 10 can be connected to the base 62 to be fixed in a stationary position. The device 60 can further include a carriage 64 that is moveably disposed above the mount assembly 10 and the base 62. The carriage 64 can include interconnected vertical and horizontal tubes or bars as a frame. The impactor 66 (i.e., head, impact object, etc.) can be fixed to the carriage 64 and can be suspended from the carriage 64.

The carriage 64 and impactor 66 can move in a vertical direction as a unit toward and away from the base 62. In some embodiments, the carriage 64 can be released such that the carriage 64 and impactor 66 freely fall toward the base 62 due to gravity. It will be appreciated that the carriage 64 and impactor 66 can travel along a substantially straight, linear path. The carriage 64 and impactor 66 are shown in broken lines in a raised position (i.e., starting position) in FIG. 3, and the carriage 64 and impactor 66 are shown in solid lines in a lowered position (i.e., impacting position) in FIG. 3. It will be appreciated that the carriage 64 and impactor 66 are spaced from the apparel 11 when in the raised position, and the impactor 66 is in contact with the apparel 11 when in the lowered position. (For purposes of discussion, the "lowered position" will be considered to be the position at which the impactor 66 makes initial contact with the apparel 11; however, it will be appreciated that the impactor 66 could travel even lower due to the apparel 11 being driven into the deformable member 12. Thus, in additional embodiments, the "lowered position" could be the lowest point of travel of the impactor 66 away from the raised position.)

It will be appreciated that the device 60 could operate or could be configured differently without departing from the scope of the present disclosure. For instance, the device 60 could include a carriage 64 that swings or otherwise rotates about an axis to impact the apparel 11. Also, the device 60 could include an actuator (e.g., pneumatic or hydraulic actuator, etc.) that drives the impactor 66 toward the apparel 11 in some embodiments. Moreover, the carriage 64 could be configured to reciprocate between the raised and lowered positions to repeatedly impact the apparel 11. Also, in some embodiments, the apparel 11 could be substantially centered over the longitudinal axis X of the mount assembly 10 and the impactor 66 could be configured to travel along a vector that intersects the axis X; however, the apparel 11 and/or the mounting assembly 10 could be disposed relative to the impactor 66 such that the vector of travel of the impactor 66 is perpendicularly spaced away from the axis X of the mount assembly 10. In these embodiments, the testing could be configured for simulating glancing blows on the apparel 11, for detecting the effects of impacting the edges of the apparel 11 on the deformable member 12, for detecting shear loads on the deformable member 12, etc. Still further, the impact testing device 60 can be a commercially available machine, such as the TWIN WIRE™ Impact Testing tower or rig available from Cadex, Inc. of Quebec, Canada.

Also, the impact testing device 60 can be configurable for varying testing parameters in a predetermined manner. For instance, the impactor 66 can be interchangeable with impactors 66 of different weights. Thus, if a lighter impactor 66 is used, there can be less impact energy when impacting the apparel 11. On the contrary, if a heavier impactor 66 is used, there can be more impact energy. Also, the impactor 66 can be interchangeable with impactors 66 of different shapes and sizes. For instance, the bulbous impactor 66 shown in FIG. 3 could be replaced by a wedge-shaped or tapered impactor 66 or an impactor 66 of another shape. Thus, the area of contact between the impactor 66 and the apparel 11 can be changed.

Additionally, the stroke of the impactor 66 (i.e., the linear distance from its raised position to its lowered position) can be selectively varied to thereby vary the impact energy delivered by the impactor 66 to the apparel 11.

Additionally, as shown in FIG. 3, there can be a first sensor 56 that is a thin, flexible sheet or film-type of sensor. The first sensor 56 can define an outer peripheral edge 90 as shown. The first sensor 56 can also include a plurality of sensing elements, such as strain gauges, and the like, that are distributed evenly across the first sensor 56. Impacting the first sensor 56 can trigger the sensing elements to output a corresponding electrical signal. The first sensor 56 can also be used as a pressure sensor, wherein the first sensor 56 detects the distribution of pressure (force divided by area) across the first sensor 56. Also, the first sensor 56 can be configured to detect how the distribution of pressure changes over time. Moreover, the first sensor 56 can be operable for detecting temporal, local, peak, and spatial loads on and across the outer surface 16 of the deformable member 12. The sensor 56 can additionally be operable to detect how the load on the outer surface 16 changes over time (e.g., during initial compression and deformation through resilient recovery of the deformable member 12). Moreover, the first sensor 56 can be used as an impact area sensor, wherein the first sensor 56 detects how much surface area of the apparel 11 impacted the sensor 56 due to the impactor 66 impacting the apparel 11. Additionally, in some embodiments, the first sensor 56 can be a commercially-available pressure sensor from Tekscan, Inc. of Boston, Mass.

The first sensor 56 can be disposed between the inner surface 13 of the article of apparel 11 and the outer surface 16 of the deformable member 12 as shown in FIG. 3. Accordingly, the effects of the apparel 11 being impacted into the sensor 56 can be accurately correlated to the effects of the apparel 11 being impacted into the outer surface 16 of the deformable member 12. Although the first sensor 56 is shown to be slightly larger in area than the apparel 11 in FIG. 3, it will be appreciated that the sensor 56 could have approximately the same area and that the edges 90, 96 of the sensor 56 and the apparel 11 could be substantially aligned for testing in some embodiments. Also, the sensor 56 could have a smaller area than the apparel 11 in some embodiments.

One or more sensors 54 can also be operably supported by the carriage 64. For instance, in the embodiments illustrated in FIG. 3, a second sensor 57 can be operatively connected to the carriage 64 for detecting characteristics of the carriage 64 and/or impactor 66. In some embodiments, the second sensor 57 can be an accelerometer for detecting accelerations and decelerations of the carriage 64 and impactor 66 during testing as will be discussed.

Furthermore, one or more sensors 54 can be operably supported by the base 62. For instance, a third sensor 59 can be operably supported by the base 62 and can detect impact effects. For instance, in some embodiments, the third sensor 59 can be a force sensor that detects a force input to the base 62 due to the impactor 66 impacting the apparel 11.

It will be appreciated that there can be additional sensors 54 as well. For instance, the testing device 60 can include a velocity sensor in some embodiments for detecting the velocity of the impactor 66 (e.g., detecting terminal velocity upon initially impacting apparel 11).

The sensors 56, 57, 59 can be operably connected to a processor 58, such as a known data acquisition device (DAQ), via a hardwired or wireless communication. The processor 58 can be embodied on a computer, such as a desktop computer, laptop computer, tablet, etc. The processor 58 can include known software, programmed logic, hardware, etc. for receiving data from the sensors 56, 57, 59, processing the data, and outputting the data for the user. For instance, the processor 58 can be used to display the data graphically on a monitor or other display, the processor 58 can output hard-copies of the data on a printer, etc.

Use of the impact testing device 60 will now be discussed. It is assumed that the carriage 64 and impactor 66 are in the raised position (shown in phantom in FIG. 3), the mount assembly 10 is attached to the base 62 of the device 60, the article of apparel 11 is mounted atop the first sensor 56, and the first sensor 56 is layered over the deformable member 12.

During testing, the carriage 64 can be released to freely fall toward the article of apparel 11. As a result of impact, the impactor 66 and apparel 11 can be driven into the deformable member 12 such that the deformable member 12 resiliently deforms. The resiliency of the deformable member 12 can cause the member 12 to recover to its natural shape.

The sensor(s) 54 can detect effects of this impact and/or recovery. The sensor(s) can transmit respective data to the processor 58, which can consequently gather, process, and output data corresponding to the impact effects on the apparel 11 and the mount assembly 10.

Figure 5:
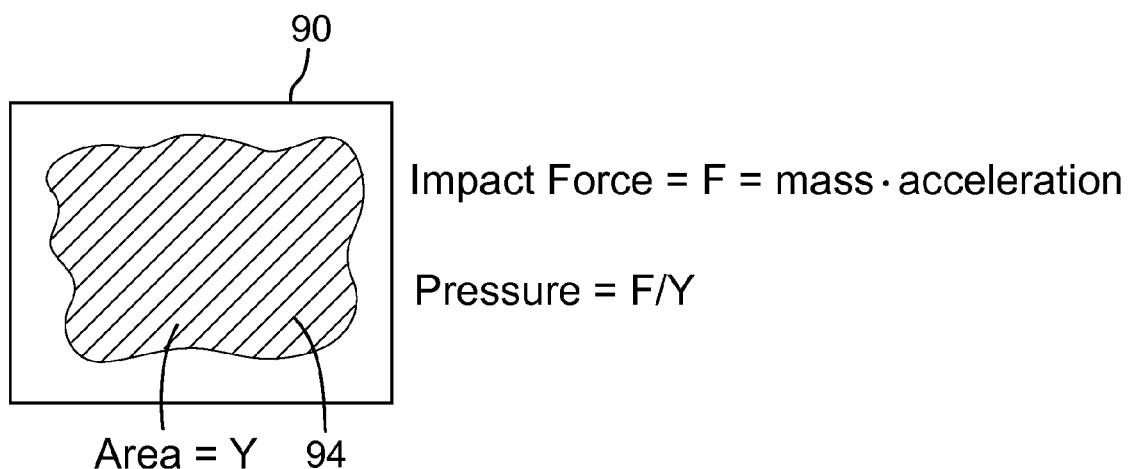
FIG. 5 is a schematic diagram of impact effects that are detected and processed from an impact test using the mount assembly of FIG. 1.

Specifically, the first sensor 56 can detect the amount of area (surface area) of the protective apparel 11 that impacts the deformable member 12 due to the impactor 66 impacting the apparel 11. The second sensor 57 can also detect the acceleration of the impactor 66. The processor 58 can calculate the force of impact of the impactor 66 using the acceleration data from the second sensor 57 and the known mass of the impactor 66 (Force=mass×acceleration). Using this calculated impact force and impact area detected by the first sensor 56, the pressure on the deformable member 12 can be calculated (Pressure=Force/Area). This is illustrated schematically in FIG. 5, wherein an impact area 94 (Y) detected by the first sensor 56 is illustrated. As shown, the impact area 94 can be disposed within the edge 90 of the first sensor 56 (e.g., due to flexure of the apparel 11). As mentioned, the second sensor 57 can detect acceleration of the impactor 66, and impact force (F) can be calculated from this acceleration. Then, impact pressure can be calculated by dividing the impact force (F) by the impacted area (Y).

In some embodiments, the third sensor 59 can be used to detect impact force (F) as well. Additionally, both the second sensor 57 and third sensor 59 can redundantly detect impact force, and the detected impact forces can be compared by the processor 58 to ensure that the sensors 57, 59 are working accurately.

Figure 6:
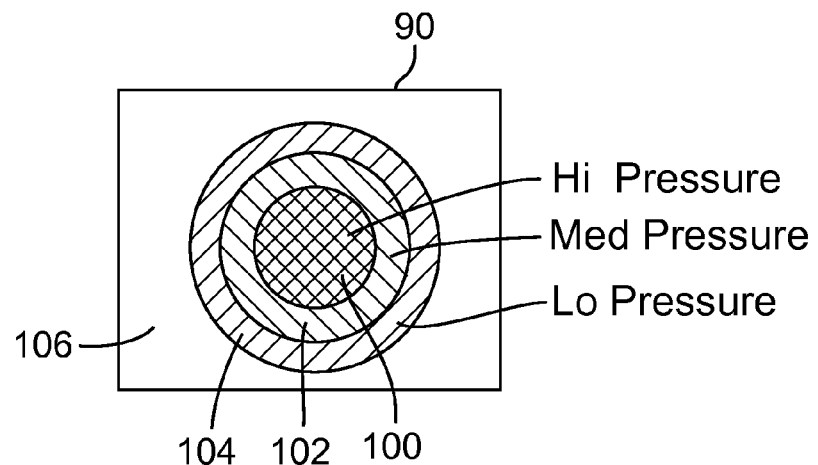
FIG. 6 is a schematic pressure map detected from an impact test using the mount assembly of FIG. 1.

Moreover, in some embodiments, represented schematically in FIG. 6, one or more sensors 54 can detect a distribution of load across the deformable member 12. For instance, as shown in FIG. 6, the first sensor 56 can detect the distribution of pressure across the first sensor 56 (within the edge 90 of the first sensor 56). Stated differently, the first sensor 56 can detect a pressure map across the first sensor 56. In the illustrated embodiments, the first sensor 56 can detect a first area 100 of higher pressure, a second area 102 of medium pressure, and a third area 104 of lower pressure. A fourth area 106 can be detected as receiving little to no pressure due to impact. Thus, the first sensor 56 can detect areas where loading is concentrated. Moreover, as discussed above, the sensor 56 can be used to detect how loading changes over time.

Figure 4:
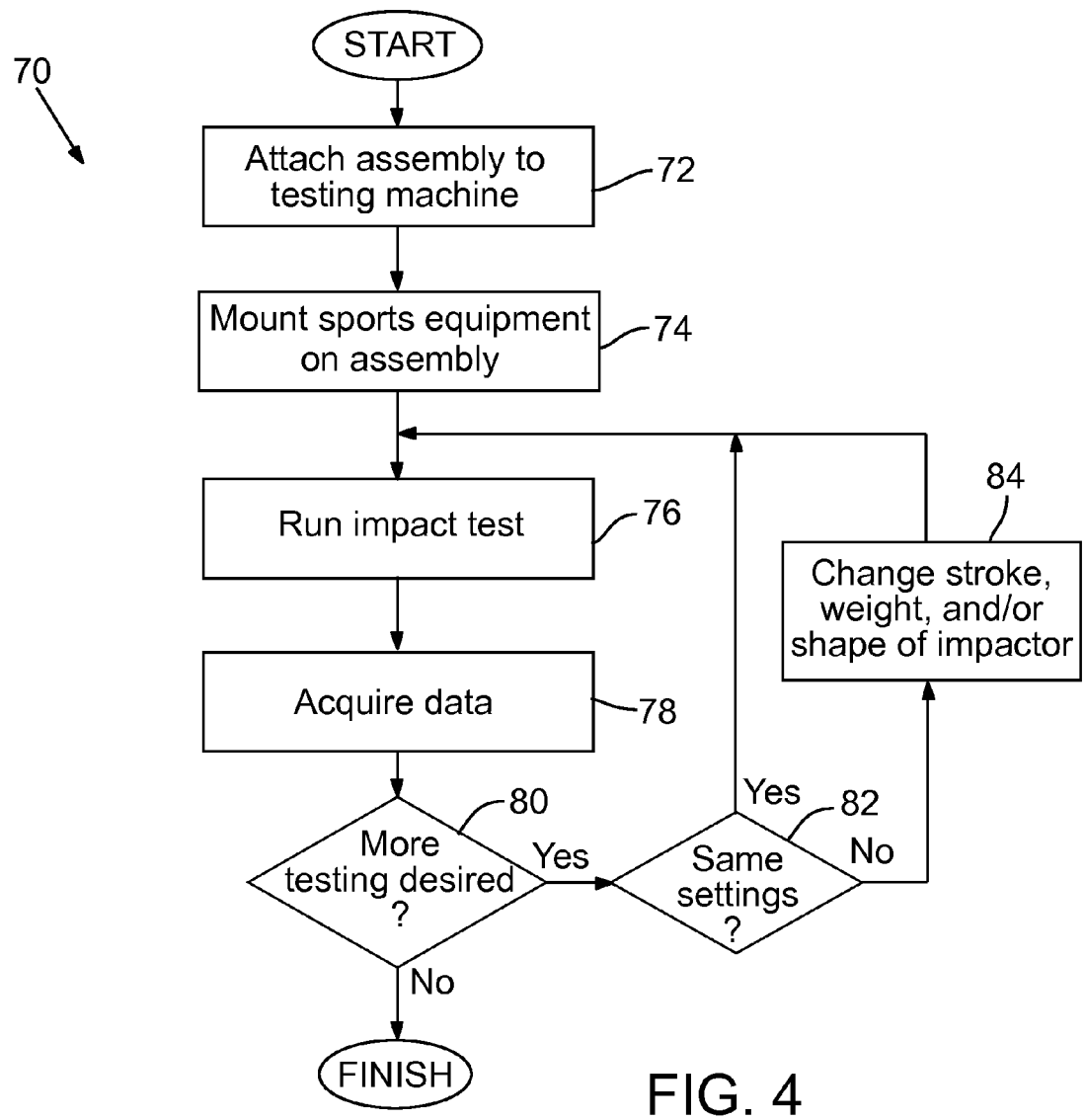
FIG. 4 is a flowchart of various exemplary embodiments of a method of impact testing using the mount assembly of FIG. 1.

Referring now to FIG. 4, a method 70 of impact testing the article of apparel 11 using the mount assembly 10 is illustrated according to various exemplary embodiments. As shown, the method 70 can begin in block 72, wherein the mount assembly 10 is mounted on the impact testing device 60. Then, in block 74, the article of apparel 11 (identified as "sports equipment" in FIG. 4) can be mounted onto the outer surface 16 of the deformable member 12. In some embodiments, the apparel 11 can be simply supported on the outer surface 16 without additional straps, fasteners, or other similar devices. However, in other embodiments, straps, fasteners, or other devices can extend from the apparel 11 and can secure to one of the projections 24 to substantially fix the apparel 11 to the deformable member 12. Also, as mentioned above, the apparel 11 can be nested to the outer surface 16 in preparation for impact testing.

Next, in block 76, the user can run the impact test 76. As described above, the carriage 64 and impactor 66 can drop toward the apparel 11 such that the impactor 66 impacts the apparel 11. The mass of the impactor 66, the stroke of the impactor 66, and other parameters can be selected such that the impactor 66 imparts predetermined impact energy on the apparel 11 and the mount assembly 10. For instance, the mass of the impactor 66 can be from approximately one kilogram (1 kg) to approximately 5 kilograms (5 kg), the stroke of the impactor 66 can be from approximately thirteen centimeters (13 cm) to approximately two meters (2 m), and the impact energy can be from between approximately three Joules (3 J) to approximately one hundred Joules (100 J).

Then, in block 78, the impact effects (e.g., pressure distribution on the outer surface 15 during the impact, accelerations, decelerations, impact forces, etc.) can be detected by the sensors 54, and corresponding data can be processed and output by the processor 58.

Next, in decision block 80, it can be determined whether more testing is desired (i.e., additional test cycles may be desired). For instance, the user may want to collect load data from several test cycles to increase the accuracy of the results. The same test parameters can be used during each cycle of testing. Also, the user may want to run the impact test several times using different test parameters. If testing is complete (i.e., block 80 answered negatively), then the method 70 can finish. However, if more testing is desired (i.e., block 80 answered positively), then decision block 82 can follow.

In block 82, the user can determine whether the test settings (i.e., test parameters) should remain the same as in the previous test. If the settings are to remain the same (i.e., block 82 answered positively), then the method 70 can loop back to block 76. However, if the test settings are to be varied (i.e., block 82 answered negatively), then block 84 can follow.

In block 84, the user can reconfigure the testing device 60 such that the apparel 11 and mount assembly 10 are subject to different impact energy from the impactor 66. For instance, as mentioned above, the impactor 66 used in the previous test can be interchanged with another impactor 66 of different weight and/or shape. Alternatively or in addition to these changes, the stroke of the carriage 64 and impactor 66 can be varied. More specifically, the initial, raised position of the carriage 64 (and, thus, the amount of travel of the impactor 66 during the test) can be adjusted to be closer or farther away from the apparel 11 as compared with the previous test. Then, the method 70 can loop back to block 76.

Accordingly, the impactor 66 can impact the apparel 11 repeatedly in block 76, and data can be acquired for each repetition in block 78. In some embodiments of the method 70, block 72 and block 74 can be completed, and then blocks 76, 78, 80, 82 can repeat (i.e., loop) three times for a single article of apparel 11 to complete a single cycle of testing. In this embodiment of the method 70, the shape and/or mass of the impactor 66 can be the same for all three impacts against the apparel 11. Furthermore, the stroke of the impactor 66 can be the same for all three impacts. In other words, block 82 can be answered affirmatively during each of the three cycles (repetitions). Accordingly, the impact energy can be approximately the same for all three impacts. Moreover, the impactor 66 can impact the apparel 11 at equal time intervals (e.g., approximately 1 minute between each of the three impacts) to allow sufficient recovery and attenuation of any impact vibrations within the deformable member 12. Additionally, the impactor 66 can be configured to impact approximately the same area on the apparel 11 during each of these three impacts. Impact data can be acquired for each of the three impacts during block 78 of the method 70, and the data can be averaged for greater accuracy.

Accordingly, the testing method 70 can be run to obtain information about how the apparel 11 and mount assembly 10 perform when subjected to impact from the impactor 66. Specifically, the distribution of pressure across the outer surface 16 due to impacting the apparel 11 can be detected. Since the mount assembly 10 is configured to simulate the anatomy (here, an anatomical thigh), the test data can be used to discover how well the apparel 11 protects a person's body during sporting activities, etc. Testing can be conducted to simulate real-world impact conditions such that the data can be very accurate. Accordingly, the apparel 11 can be designed, configured, and tested to better protect the wearer's body.

Data can also be gathered using the method 70 in a series of impact tests on multiple mount assemblies 10 of different sizes. For instance, the same-sized apparel 11 can be mounted on mount assemblies 10 having deformable members 12 of different radii, and the test method 70 can be run on each. As such, it can be determined how the apparel 11 protects anatomical thighs of different sizes, for instance. On the other hand, differently-sized apparel 11 could be impact tested on mount assemblies 10 of the same size using the test method 70. Accordingly, it can be determined how the size of the apparel 11 affects impacting of the anatomical thigh, for instance.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of impact testing an article of protective equipment comprising:
  mounting the article of protective equipment on a deformable member;
  providing a pressure sensor between the article of protective equipment and an outer surface of the deformable member;
  impacting the article of protective equipment with an impact object; and
  detecting an effect of impact on the deformable member due to impacting the article of protective equipment with the impact object,
    wherein detecting the effect of impact includes detecting a distribution of impact load across an area of the deformable member,
    wherein detecting the distribution of impact load includes detecting a distribution of impact load across the outer surface of the deformable member, and
    wherein detecting the distribution of load across the outer surface of the deformable member includes correlating a distribution of load across the pressure sensor to the distribution of load across the outer surface of the deformable member.

2. The method of claim 1, wherein mounting the article of protective equipment includes nesting the article of protective equipment to a convexly curved outer surface of the deformable member.

3. The method of claim 2, wherein the deformable member has a resilience that substantially matches a resilience of a natural thigh tissue.

4. The method of claim 1, wherein impacting the article of protective equipment includes impacting the article of protective equipment with the impact object repeatedly, and wherein detecting the effect of impact includes detecting the effect of impact on the deformable member for each repetition of impacting the article of protective equipment.

5. The method of claim 4, wherein impacting the article of protective equipment includes impacting the article of protective equipment repeatedly at approximately equal time intervals.

6. The method of claim 4, wherein impacting the article of protective equipment includes impacting the article of protective equipment repeatedly with approximately the same predetermined impact energy.

7. The method of claim 1, wherein impacting the article of protective equipment includes impacting the article of protective equipment with between approximately three Joules (3 J) and one hundred Joules (100 J) of impact energy.

8. The method of claim 1, further comprising providing an impact area sensor that is configured to detect an impact area of the protective equipment on the deformable member, and further comprising providing an accelerometer that is configured to detect an acceleration of the impact object, and wherein detecting the effect of impact includes detecting an impact force from the acceleration and dividing the impact force over the impact area.

9. The method of claim 1, wherein impacting the article of protective equipment includes releasing the impact object to fall under a force of gravity toward the article of protective equipment.

10. The method of claim 9, wherein releasing the impact object includes allowing the impact object to fall along a substantially straight, linear path toward the article of protective equipment.

11. The method of claim 1, further comprising resiliently deforming the deformable member as a result of impacting the article of protective equipment with the impact object.

12. The method of claim 1, further comprising forming the deformable member.

13. A method of impact testing an article of protective equipment comprising:
    mounting the article of protective equipment on a deformable member that is supported by a substantially rigid core member;
    providing an impact area sensor that is configured to detect an impact area of the protective equipment on the deformable member;
    providing an accelerometer that is configured to detect an acceleration of an impact object, which is usable to impact the article of protective equipment;
    impacting the article of protective equipment with the impact object to thereby resiliently deform the deformable member; and
    detecting a pressure on an outer surface of the deformable member due to impacting the article of protective equipment with the impact object, wherein detecting the pressure on the outer surface includes detecting an impact force from the acceleration and dividing the impact force over the impact area.

14. The method of claim 13, further comprising detecting a distribution of load across the outer surface of the deformable member due to impacting the article of protective equipment with the impact object.

15. The method of claim 13, wherein impacting the article of protective equipment includes impacting the article of protective equipment with between approximately three Joules (3 J) and one hundred Joules (100 J) of impact energy.

16. A method of impact testing an article of protective equipment comprising:
    mounting the article of protective equipment on a deformable member that is supported by a substantially rigid core member;
    providing a pressure sensor between the article of protective equipment and an outer surface of the deformable member;
    impacting the article of protective equipment with an impact object at a predetermined impact energy during a first cycle to thereby drive the article of protective equipment toward the deformable member and to resiliently deform the deformable member;
    detecting a first pressure on the outer surface of the deformable member due to impacting the article of protective equipment with the impact object during the first cycle, wherein detecting the first pressure includes correlating a distribution of load across the pressure sensor during the first cycle to the distribution of load across the outer surface of the deformable member;
    impacting the article of protective equipment with the impact object at the predetermined impact energy during a second cycle to thereby drive the article of protective equipment toward the deformable member and to resiliently deform the deformable member; and
    detecting a second pressure on the outer surface of the deformable member due to impacting the article of protective equipment with the impact object during the second cycle, wherein detecting the second pressure includes correlating a distribution of load across the pressure sensor during the second cycle to the distribution of load across the outer surface of the deformable member.

* * * * *